(12) United States Patent
Mehta et al.

(10) Patent No.: US 7,517,905 B2
(45) Date of Patent: *Apr. 14, 2009

(54) SUBSTITUTED AZABICYCLO HEXANE DERIVATIVES AS MUSCARINIC RECEPTOR ANTAGONISTS

(75) Inventors: Anita Mehta, Plainfield, IL (US); Bruhaspathy Miriyala, Aspinwall, PA (US); Sudershan Kumar Arora, Maharashtra (IN); Jang Bahadur Gupta, Dusseldorf (DE)

(73) Assignee: Ranbaxy Laboratories Limited, Gurgaon (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/552,456

(22) PCT Filed: Apr. 9, 2003

(86) PCT No.: PCT/IB03/01288

§ 371 (c)(1),
(2), (4) Date: Aug. 14, 2006

(87) PCT Pub. No.: WO2004/089898

PCT Pub. Date: Oct. 21, 2004

(65) Prior Publication Data

US 2006/0281805 A1    Dec. 14, 2006

(51) Int. Cl.
    *A61K 31/403* (2006.01)
    *C07D 209/52* (2006.01)
(52) U.S. Cl. ................................ 514/412; 548/515
(58) Field of Classification Search ........... 548/515; 514/412
    See application file for complete search history.

(56) References Cited

U.S. PATENT DOCUMENTS

| | | | | |
|---|---|---|---|---|
| 2,490,714 | A | 12/1949 | Searle | 260/239 |
| 3,176,019 | A | 3/1965 | Campbell et al. | 260/293.43 |
| 5,001,160 | A | 3/1991 | McPherson et al. | 514/255 |
| 5,164,402 | A | 11/1992 | Brighty | 514/300 |
| 5,179,108 | A | 1/1993 | George et al. | 514/319 |
| 5,281,601 | A | 1/1994 | Cross et al. | 514/320 |
| 5,397,800 | A | 3/1995 | Alker et al. | 514/413 |
| 5,559,269 | A | 9/1996 | Johansson et al. | 564/443 |
| 5,948,792 | A | 9/1999 | Tsuchiya et al. | 514/317 |
| 6,130,232 | A | 10/2000 | Mase et al. | 514/318 |
| 6,174,900 | B1 | 1/2001 | Okada et al. | 514/317 |
| 6,313,312 | B1 | 11/2001 | Banks et al. | 548/452 |
| 7,288,562 | B2 | 10/2007 | Mehta et al. | 514/412 |
| 2003/0105071 | A1 | 6/2003 | Cuny et al. | 514/210.2 |
| 2003/0162780 | A1 | 8/2003 | Brotherton-Pleiss et al. | 514/235.5 |
| 2003/0171362 | A1 | 9/2003 | Madera et al. | 514/218 |
| 2006/0287380 | A1 | 12/2006 | Salman et al. | 514/412 |

FOREIGN PATENT DOCUMENTS

| | | |
|---|---|---|
| CA | 2155320 | 8/1993 |
| EP | 0 325 571 | 7/1989 |
| EP | 0 388 054 | 9/1990 |
| EP | 0 413 455 | 2/1991 |
| EP | 0 613 232 | 8/1994 |
| EP | 0 801 067 | 10/1997 |
| EP | 0 823 423 | 2/1998 |
| EP | 0 863 141 | 9/1998 |
| EP | 0 930 298 | 7/1999 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | WO 97/45414 | 12/1997 |
| WO | WO 98/00016 | 1/1998 |
| WO | WO 98/00109 | 1/1998 |
| WO | WO 98/00132 | 1/1998 |
| WO | WO 98/00133 | 1/1998 |
| WO | WO 98/05641 | 2/1998 |
| WO | WO 98/29402 | 7/1998 |
| WO | 98/53814 | 12/1998 |
| WO | 99/43657 | 9/1999 |
| WO | 01/42212 | 6/2001 |
| WO | WO 01/42213 | 6/2001 |
| WO | WO 01/47893 | 7/2001 |
| WO | WO 01/90081 | 11/2001 |
| WO | WO 01/90082 | 11/2001 |
| WO | WO 02/00652 | 1/2002 |

(Continued)

OTHER PUBLICATIONS

Morissette et al. Advanced Drug Delivery Reviews 2004, 56, 275-300.*

(Continued)

*Primary Examiner*—Kamal A Saeed
*Assistant Examiner*—Jason M Nolan
(74) *Attorney, Agent, or Firm*—Jayadeep R. Deshmukh, Esq.; George E. Heibel, Esq.

(57) ABSTRACT

This invention relates to the derivatives of substituted azabicyclo hexanes. The compounds of this invention can function as muscarinic receptor antagonists and can be used for the treatment of various diseases of the respiratory, urinary and gastrointestinal systems mediated through muscarinic receptors. The invention also relates to a process for the preparation of the compounds of the present invention, pharmaceutical compositions containing the compounds of the present invention and the methods of treating the diseases mediated through muscarinic receptors.

12 Claims, No Drawings

FOREIGN PATENT DOCUMENTS

| WO | WO 02/04402 | 1/2002 |
|---|---|---|
| WO | WO 02/006241 | 1/2002 |
| WO | WO 02/051841 | 7/2002 |
| WO | WO 02/053564 | 7/2002 |
| WO | WO 03/033495 | 4/2003 |
| WO | WO 03/048124 | 6/2003 |
| WO | WO 03/048125 | 6/2003 |
| WO | WO 2004/004629 | 1/2004 |
| WO | WO 2004/005252 | 1/2004 |
| WO | WO 2004/014363 | 2/2004 |
| WO | WO 2004/014853 | 2/2004 |
| WO | WO 2004/018422 | 3/2004 |
| WO | WO 2004/052857 | 6/2004 |
| WO | WO 2004/056767 | 7/2004 |
| WO | WO 2004/056810 | 7/2004 |
| WO | WO 2004/056811 | 7/2004 |
| WO | WO 2004/067510 | 8/2004 |
| WO | WO 2004/069835 | 8/2004 |
| WO | WO 2004/089363 | 10/2004 |
| WO | WO 2004/089899 | 10/2004 |
| WO | WO 2004/089900 | 10/2004 |
| WO | WO 2005/092341 | 10/2005 |
| WO | WO 2006/003587 | 1/2006 |
| WO | WO 2006/035282 | 4/2006 |
| WO | WO 2006/064304 | 6/2006 |

OTHER PUBLICATIONS

Kubo et al., "Cloning, sequencing and expression of complementary DNA encoding the muscarinic acetylcholine receptor", *Nature*, 323(2):411-416 (1986).

Bonner et al., "Identification of a Family of Muscarinic Acetylcholine Receptor Genes", *Science*, 237:527-531 (1987).

Eglen et al., "Muscarinic receptor ligands and their theraputic potential", *Current Opinion in Chemical Biology*, 3:426-432 (1999).

Eglen et al., "Theraputic opportunities from muscarinic receptor research", *Trends in Pharmacological Sciences*, 22(8):409-414 (2001).

Felder et al., "Theraputic Opportunities for Muscarinic Receptors in the Central Nervous System", *Journal of Medicinal Chemistry*, 43(23):4333-4353 (2000).

Broadley and Kelly, "Muscarinic Receptor Agonists and Antagonists", *Molecules*, 6:142-193 (2001).

Birdsall et al., "Muscarinic receptors: it's a knockout", *Trends in Pharmacological Sciences*, 22(5):215-219 (2001).

de Groat and Yoshimura, "Pharmacology of the Lower Urinary Tract", *Annual Review of Pharmacology and Toxicology*, 41:691-721 (2001).

Steers, "The future direction of neuro-urology drug research", *Current Opinion in CPNS Investigational Drugs*, 2(3):268-282.

Chapple, "Muscarinic receptor antagonists in the treatment of overactive bladder", *Urology*, 55(Suppl. 5A):33-46 (2000).

Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).

Sagara et al., "Cyclohexylmethylpiperidinyltriphenylpropioamide: A Selective Muscarinic M3 Antagonist Discriminating against the Other Receptor Subtypes", *Journal of Medicinal Chemistry*, 45:984-987 (2002).

Braish et al., "Construction of the (1α,5α,6α)-6-Amino-3-azabicyclo[3.1.0]hexane Ring System", *Synlett*, 1100-1102 (1996).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Cheng and Prusoff, "Relationship between the inhibition constant ($K1$) and the concentration of inhibitor which causes 50 per cent inhibition ($I50$) of an enzymatic reaction", *Biochemical Pharmacology*, 22:3099-3108 (1973).

Andersson et al, "Asymmetric Total Synthesis of (+)-Tolterodine, a New Muscarinic Receptor Antagonist, via Copper-Assisted Asymmetric Conjugate Addition of Aryl Gridngard Reagents to 3-Phenyl-prop-2-enoyl-oxazolidinones", *Journal of Organic Chemistry*, 63(22): 8067-8070 (1998).

Brighty et al., "Synthesis of (1α, 5α, 6α)-6-Amino-3-azabicyclo[3.1.0]hexane, a Novel Achiral Diamine", *Synlett*, 1097-1099 (1996).

Grover et al., "Chiral Mandelic Acid Template Provides a Highly Practical Solution for (S)-Oxybutynin Synthesis", *Journal of Organic Chemistry*, 65:6283-6287 (2000).

Shacklett and Smith, "The Preparation of Substituted Benzilic Acids", *Journal of the American Chemical Society*, 75:2654-2657 (1953).

Nkpa and Chedekel, "Mechanistic Studies on the Addition of Cysteine to 3,4-Dihydroxyphenylalanine", *Journal of Organic Chemistry*, 46:213-215 (1981).

Kadin and Cannon, "Esters of N-Methyl-3-hydroxypiperidine Having Psychotomimetic Activity. II", *Journal of Organic Chemistry*, 27:240-245 (1962).

Weinstock et al., "A General, One-Step Synthesis of α-keto Esters", *Synthetic Communications*, 11(12):943-946 (1981).

Vogel et al., 1996. *Vogel's Textbook of Practical Organic Chemistry*. 5th Edition. USA: Prentice Hall, 1046-1047.

Bundgaard, H., 1985. *Design of Prodrugs*. Elsevier.

Kaiser et al., "Synthesis and Antimuscarinic Activity of Some 1-Cycloalkyl-1-hydroxy-1-phenyl-3-(4-substituted piperazinyl)-2-propanones and Related Compounds", *Journal of Medicinal Chemistry*, 36(5):610-616 (1993).

Carter et al., "Analogues of Oxybutynin. Synthesis and Antimuscarinic and Bladder Activity of Some Substituted 7-Amino-1-hydroxy-5-heptyn-2-ones and Related Compounds", *Journal of Medicinal Chemistry*, 34(10):3065-3074 (1991).

Wess et al., "Muscarinic receptor subtypes mediating central and peripheral antinociception studied with muscarinic receptor knockout mice: A review", *Life Sciences*, 72:2047-2054 (2003).

O'Neill, "Unusual suspect for antipsychotic-induced diabetes", *Drug Discovery Today*, 10(20):1338 (2005).

Michel and Hegde, "Treatment of the overactive bladder syndrome with muscarinic receptor antagonists - a matter of metabolites∞", *Naunyn-Schmiedeberg's Arch Pharmacol*, 374:79-85 (2006).

Latifpour et al., "Effects of Experimental Diabetes on Biochemical and Functional Characteristics of Bladder Muscarinic Receptors", *The Journal of Pharmacology and Experimental Therapeutics*, 248(1):81-88 (1989).

Carrier and Aronstam, "Altered Muscarinic Receptor Properties and Function in the Heart in Diabetes", *The Journal of Pharmacology and Experimental Therapeutics*, 242(2):531-535 (1987).

Ahrén et al., "Blockade of muscarinic transmission increases the frequency of diabetes after low-dose alloxan challenge in the mouse", *Diabetologia*, 39:383-390 (1996).

Abrams et al., "Muscarinic receptors: their distribution and function in body systems, and the implications for treating overactive bladder", *British Journal of Pharmacology*, 148(5):565-578 (2006).

Patani and LaVoie, "Bioisosterism: A Rational Approach in Drug Design," *Chem. Rev.* 96, (1996) pp. 3147-3176.

* cited by examiner

SUBSTITUTED AZABICYCLO HEXANE DERIVATIVES AS MUSCARINIC RECEPTOR ANTAGONISTS

FIELD OF THE INVENTION

This invention relates to derivatives of substituted azabicyclo hexanes.

The compounds of this invention can function as muscarinic receptor antagonists, and can be used for the treatment of various diseases of the respiratory, urinary and gastrointestinal systems mediated through muscarinic receptors.

The invention also relates to a process for the preparation of the compounds of the present invention, pharmaceutical compositions containing the compounds of the present invention and the methods of treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; *Science*, 1987; 237: 527).

A review in *Current Opinions in Chemical Biology*, 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in *J. Med. Chem.*, 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules* 2001, 6: 142.

N. J. M. Birdsall et. al. in *Trends in Pharmacological Sciences*, 2001; 22: 215 have also summarized the recent developments on the role of different muscarinic receptor subtypes using different muscaranic receptors of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of *Pharmacological Toxicol.*, 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W. D. Steers et. al. in *Curr. Opin. Invest. Drugs*, 2: 268, C. R. Chapple et. al. in *Urology* 55: 33), Steers W D, Barrot D M, Wein A J, 1996, Voiding dysfunction: diagnosis classification and management. In "Adult and Pediatric Urology," ed. J Y Gillenwatter, J T Grayhack, S S Howards, J W Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Numbers 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other close art references.

A report in *J. Med. Chem.*, 2002; 44:984, describes cyclohexylmethyl piperidinyl triphenylpropioamide derivatives as selective $M_3$ antagonist discriminating against the other receptor subtypes.

PCT applications WO 98/00109; 98/00132; 98/00133 and 98/00016 disclose isomers of glycopyrolate.

SUMMARY OF THE INVENTION

The present invention provides substituted azabicyclo hexanes as muscarinic receptor antagonists which are useful as safe and effective therapeutic or prophylactic agents for the treatment of various diseases of the respiratory, urinary and gastrointestinal systems, and a process for the syntheses of these compounds.

The invention also provides pharmaceutical compositions containing the compounds, and which may also contain pharmaceutically acceptable carriers, excipients or diluents which are useful for the treatment of various diseases of the respiratory, urinary and gastrointestinal systems.

The invention also includes within its scope prodrugs of the compounds. In general, such prodrugs are functionalized derivatives of these compounds which readily get converted in vivo into the defined compounds. Conventional procedures for the selection and preparation of suitable prodrugs are known to the artisan of ordinary skill in the art.

The invention also includes the enantiomers, diastereomers, N-oxides, polymorphs, pharmaceutically acceptable salts and pharmaceutically acceptable solvates, esters, and metabolites of these compounds having the same type of activity.

The invention further includes pharmaceutical compositions comprising the compounds of the present invention, their metabolites, esters, enantiomers, diastereomers, prodrugs, N-oxides, polymorphs, pharmaceutically acceptable salts or pharmaceutically acceptable solvates, in combination with a pharmaceutically acceptable carrier and optionally included excipients.

In accordance with one aspect of the present invention, there are provided compounds having the structure of Formula I:

Formula I

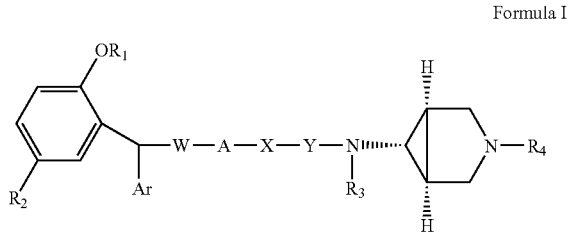

and their pharmaceutically acceptable salts, pharmaceutically acceptable solvates, esters, enantiomers, diastereomers, N-oxides, polymorphs, prodrugs or metabolites, wherein Ar represents an aryl or a heteroaryl ring having 1-2 hetero atoms selected from the group consisting of oxygen, sulphur or nitrogen atoms, the aryl or heteroaryl rings may be unsubstituted or substituted by one to three substituents independently selected from lower alkyl ($C_1$-$C_4$), trifluoromethyl, methylenedioxy, cyano, hydroxy, halogen (e.g. F, Cl, Br, I), nitro, lower alkoxy ($C_1$-$C_4$), amino or lower alkylamino ($C_1$-$C_4$);

$R_1$ represents hydrogen, lower alkyl ($C_1$-$C_4$), lower alkenyl ($C_1$-$C_4$), lower alkynyl ($C_1$-$C_4$), aryl or aralkyl;

$R_2$ represents hydrogen or lower alkyl ($C_1$-$C_4$);

A represents $(CH_2)_n$ or CO, wherein n is an integer in the range of 0 to 4;

W represents $(CH_2)_p$, wherein p represents 1 to 4;

X represents O, S, NR or no atom, wherein R represents H or lower alkyl ($C_1$-$C_4$);

Y represents $CHR_5CO$, $(CH_2)_q$ or no atom, wherein $R_5$ represents hydrogen or methyl and q represents 1 to 4; and $R_3$ and $R_4$ are independently selected from hydrogen, straight chain or branched alkyl ($C_1$-$C_4$), cycloalkyl, $CO_2C(CH_3)_3$, optionally substituted aryl or aralkyl.

In accordance with a second aspect of the present invention, there is provided a method for treatment or prophylaxis of an animal or a human suffering from a disease or disorder of the respiratory, urinary and gastrointestinal systems, wherein the disease or disorder is associated with muscarinic receptors, comprising administering to a patient in need thereof, an effective amount of compounds as described above.

In accordance with a third aspect of the present invention, there is provided a method for treatment or prophylaxis of an animal or a human suffering from a disease or disorder associated with muscarinic receptors, comprising administering to a patient in need thereof, an effective amount of compounds as described above.

In accordance with a fourth aspect of the present invention, there is provided a method for treatment or prophylaxis of an animal or a human suffering from a disease or disorder of the urinary system which induce urinary disorders such as urinary incontinence, lower urinary tract symptoms (LUTS), etc.; respiratory system such as bronchial asthma, chronic obstructive pulmonary disorders (COPD), pulmonary fibrosis, etc.; and gastrointestinal system such as irritable bowel syndrome, obesity, diabetes and gastrointestinal hyperkinesis with compounds as described above, wherein the disease or disorder is associated with muscarinic receptors, comprising administering to a patient in need thereof, an effective amount of compounds as described above.

In accordance with a fifth aspect of the present invention, there is provided a process for preparing the compounds as described above.

The compounds of the present invention exhibit significant potency in terms of their activity, which was determined by in vitro receptor binding and functional assays and in vivo experiments using anaesthetized rabbit. The compounds that were found active in in vitro assay were tested in vivo. Some of the compounds of the present invention were found to be potent muscarinic receptor antagonists with high affinity towards $M_3$ receptors. Therefore, the present invention provides pharmaceutical compositions for treatment of diseases or disorders associated with muscarinic receptors. Compounds and compositions described herein can be administered orally or parentally.

DETAILED DESCRIPTION OF INVENTION

The compounds described herein may be prepared by the techniques well known in the art and familiar to the average synthetic organic chemist. In addition, the compounds described herein may be prepared by the following reaction sequence as depicted in

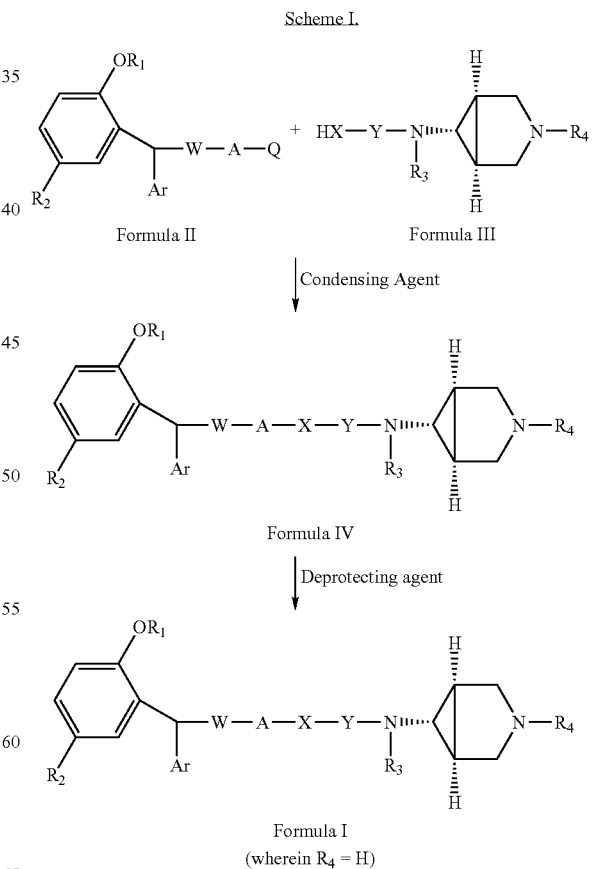

The preparation comprises condensing a compound of Formula II with the compound of Formula III wherein Ar represents an aryl or a heteroaryl ring having 1-2 hetero atoms selected from the group consisting of oxygen, sulphur or nitrogen atoms, the aryl or heteroaryl rings may be unsubstituted or substituted by one to three substituents independently selected from lower alkyl ($C_1$-$C_4$), trifluoromethyl, methylenedioxy, cyano, hydroxy, halogen (e.g., F, Cl, Br, I), nitro, lower alkoxy ($C_1$-$C_4$), amino or lower alkylamino ($C_1$-$C_4$);

$R_1$ represents hydrogen, lower alkyl ($C_1$-$C_4$), lower alkenyl ($C_1$-$C_4$), lower alkynyl ($C_1$-$C_4$), aryl or aralkyl;

$R_2$ represents hydrogen or lower alkyl ($C_1$-$C_4$);

A represents $(CH_2)_n$ or CO, wherein n is an integer in the range of 0 to 4;

W represents $(CH_2)_p$, wherein p represents 1 to 4;

X represents O, S, NR or no atom, wherein R represents H or lower alkyl ($C_1$-$C_4$);

Y represents $CHR_5CO$, $(CH_2)_q$ or no atom, wherein $R_5$ represents hydrogen or methyl and q represents 1 to 4; and $R_3$ and $R_4$ are independently selected from hydrogen, straight chain or branched alkyl ($C_1$-$C_4$), cycloalkyl, $CO_2C(CH_3)_3$, optionally substituted aryl or aralkyl;

and Q is a leaving group, for example, hydroxy, amino, O-tosyl, O-mestyl and halogen, in the presence of a condensing agent to give a protected compound of Formula IV, which on deprotection through reaction with a deprotecting agent gives the compound of Formula I.

The reaction of the compound of Formula II with a compound of Formula III to give compounds of Formula IV can be carried out in the presence of a suitable condensing agent, for example, 1-(3-dimethylamino propyl)-3-ethyl carbodiimide hydrochloride (EDC) and 1,8-diazabicyclo[5.4.0]undec-7ene (DBU).

The reaction of the compound of Formula II with a compound of Formula III to give compounds of Formula IV can be carried out in the presence of a base, for example, N-methyl morpholine (NMM), N-methyl-2-pyrrolidinone (NMP), sodium carbonate, potassium carbonate, potassium iodide, triethylamine and diisopropylamine.

The reaction of the compound of Formula II with compounds of Formula III to give compounds of Formula IV can be carried out in a suitable solvent, for example, N,N-dimethylformamide, dimethylsulphoxide, toluene, xylene, methanol and dichloromethane at a temperature ranging from about 0° C. to about 140° C.

The deprotection of the compound of Formula IV to give compounds of Formula I can be carried out with a suitable deprotecting agent, for example, palladium on carbon, trifluoroacetic acid (TEA) and hydrochloric acid.

The compounds of Formula II can be prepared by the reaction between p-methyl phenol with cinnamic acid to give the cyclized pyranone product which is then reacted with alkyl or aryl halide in a suitable base such as potassium carbonate in methanol. The resulting compound is finally hydrolyzed. The compounds of Formula II can also be prepared by the method as described in European patent application EP 0325571.

In the above scheme, where specific bases, condensing agents, deprotecting agents, solvents etc. are mentioned, it is to be understood that other bases, condensing agents, deprotecting agents, solvents etc. known to those skilled in art may be used. Similarly, the reaction temperature and duration may be adjusted according to desired needs.

An illustrative list of particular compounds which are capable of being produced by Scheme I and shown in Table 1 include:

Compound No. Chemical Name 1. 3-(2-Methoxy-5-methylphenyl)-3-phenylpropionic acid-(3-benzyl-3-azabicyclo[3.1.0]hex-6-yl-carbamoyl)methyl ester. (Compound No. 1)

2. 3-(2-Benzyloxy-5-methylphenyl)-3-phenylpropionic acid (3-benzyl-3-azabicyclo[3.1.0]hex-6-yl carbamoyl)methyl ester. (Compound No. 2)

3. N-(3-Azabicyclo[3.1.0]hex-6-yl)-3-(2-hydroxy-5-methylphenyl)-3-phenyl-1-propionic acid. (Compound No. 3)

4. N-(3-Azabicyclo[3.1.0]hex-6-yl)-3-(2-methoxy-5-methylphenyl)-3-phenyl-1-propionamide.(Compound No. 4)

5. 3-(2-Methoxy-5-methylphenyl)-3-phenylpropionic acid-4-[(3-azabicyclo [3.1.0]hex-6-yl)-ethoxy carbonylamino]butyl ester. (Compound No. 5)

6. 3-(2-Hydroxy-5-methylphenyl)-3-phenylpropionic acid-4-[(3-azabicyclo [3.1.0]hex-6-yl)-ethoxy carbonylamino] butyl ester. (Compound No. 6)

7. 3-(2-Methoxy-5-methylphenyl)-3-phenylpropionic acid-(3-azabicyclo[3.1.0]hex-6-yl carbamoyl)methyl ester. (Compound No. 7)

8. 3-(2-Hydroxy-5-methylphenyl)-3-phenylpropionic acid-(3-azabicyclo[3.1.0]hex-6-yl carbamoyl)methyl ester. (Compound No. 8)

9. N-[(3-Benzyl-3-azabicyclo[3.1.0]hex-6-yl carbamoyl)-methyl]-3-(2-hydroxy-5-methylphenyl)-3-phenyl propionamide. (Compound No. 9)

10. N-[(3-Benzyl-3-azabicyclo[3.1.0]hex-6-yl carbamoyl]-methyl]-3-(2-methoxy-5-methylphenyl)-3-phenyl propionamide. (Compound No. 10)

11. N-(3-Benzyl-3-azabicyclo[3.1.0]hex-6-yl)-3-(2-hydroxy-5-methylphenyl)-3-phenyl propionamide. (Compound No. 11)

12. 3-(2-Methoxy-5-methylphenyl)-3-phenylpropionic acid-4-[(3-benzyl-3-azabicyclo[3.1.0]hex-6-yl)ethoxy carbonylamino]butyl ester. (Compound No. 12)

13. 3-(2-Benzyloxy-5-methylphenyl)-3-phenylpropionic acid-4-[(3-benzyl-3-azabicyclo[3.1.0]hex-6-yl)-ethoxy carbonylamino]butyl ester. (Compound No. 4)

14. N-(3-Benzyl-3-azabicyclo[3.1.0]-hex-6-yl)-3-(2-methoxy-5-methylphenyl)-3-phenyl propionamide. (Compound No. 14)

15. (R or S)—N-(3-Benzyl-3-azabicyclo[3.1.0]hex-6-yl)-3-[3-(2-methoxy-5-methylphenyl)-3-phenyl propyl]amine. (Compound No. 15)

16. (R or S)—N-(3-Benzyl-3-azabicyclo[3.1.0]hex-6-yl)-3-[3-(2-hydroxy-5-methylphenyl]-3-phenyl propyl]amine. (Compound No. 16)

TABLE I

Formula I

[Structure of Formula I: aryl group with OR₁, R₂ substituents, Ar group, connected via W–A–X–Y–N(R₃) to a bicyclic amine with N–R₄]

(wherein R₂=CH₃, W=(CH₂)ₚ when p = 1, Ar is phenyl)

| Compound No. | A | X | Y | R₁ | R₃ | R₄ |
|---|---|---|---|---|---|---|
| 1 | C(=O) | O | —H₂C—C(=O)— | CH₃ | H | CH₂—C₆H₅ |
| 2 | C(=O) | O | —H₂C—C(=O)— | CH₂—C₆H₅ | H | CH₂—C₆H₅ |
| 3 | C(=O) | — | — | H | H | H |
| 4 | C(=O) | — | — | CH₃ | H | H |
| 5 | C(=O) | O | —(CH₂)₄— | CH₃ | CO₂C(CH₃)₃ | H |
| 6 | C(=O) | O | —(CH₂)₄— | H | CO₂C(CH₃)₃ | H |
| 7 | C(=O) | O | —H₂C—C(=O)— | CH₃ | H | H |
| 8 | C(=O) | O | —H₂C—C(=O)— | H | H | H |
| 9 | C(=O) | NH | —H₂C—C(=O)— | H | H | CH₂—C₆H₅ |
| 10 | C(=O) | NH | —H₂C—C(=O)— | CH₃ | H | CH₂—C₆H₅ |
| 11. | C(=O) | — | — | H | H | CH₂—C₆H₅ |
| 12. | C(=O) | O | —(CH₂)₄— | CH₃ | CO₂C(CH₃)₃ | CH₂—C₆H₅ |
| 13. | C(=O) | O | —(CH₂)₄— | CH₂—C₆H₅ | CO₂C(CH₃)₃ | CH₂—C₆H₅ |

TABLE I-continued

Formula I (wherein $R_2$=$CH_3$, W=$(CH_2)_p$ when p = 1, Ar is phenyl)

| Compound No. | A | X | Y | $R_1$ | $R_3$ | $R_4$ |
|---|---|---|---|---|---|---|
| 14. | $\overset{O}{\underset{C}{\|\|}}$ (—C(=O)—) | — | — | $CH_3$ | H | $CH_2$—$C_6H_5$ |
| 15. | $CH_2$ | — | — | $CH_3$ | H | $CH_2$—$C_6H_5$ |
| 16. | $CH_2$ | — | — | H | H | $CH_2$—$C_6H_5$ |

Compounds or composition disclosed may be administered to an animal for treatment orally, or by a parenteral route. Pharmaceutical compositions disclosed herein can be produced and administered in dosage units; each unit containing a certain amount of at least one compound described herein and/or at least one physiologically acceptable addition salt thereof The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes the enantiomers, diastereomers, N-oxides, polymorphs, solvates and pharmaceutically acceptable salts of these compounds as well as metabolites having the same type of activity. The present invention further includes pharmaceutical composition comprising the molecules of Formula I or metabolites, enantiomers, diastereomers, N-oxides, polymorphs, solvates or pharmaceutically acceptable salts thereof, in combination with pharmaceutically acceptable carrier and optionally included excipients.

The examples mentioned below demonstrate the general synthetic procedure as well as the specific preparation of preferred compounds. The examples are provided to illustrate particular aspects of the disclosure and should not be constrained to limit the scope of the present invention as defined by the claims.

EXPERIMENTAL DETAILS

Various solvents such as acetone, methanol, pyridine, ether, tetrahydrofuran, hexane and dichloromethane were dried using various drying reagents according to the procedures well known in the literature. IR spectra were recorded as nujol mulls or a thin neat film on a Perkin Elmer paragon instrument, Nuclear Magnetic Resonance (NMR) were recorded on a Varian XL-300 $MH_z$ instrument using tetramethylsilane as an internal standard.

EXAMPLE 1

Preparation of 3-(2-Methoxy-5-methylphenyl)-3-phenyl propanoic acid-(3-benzyl-3-azabicyclo[3.1.0]hexane-6-yl-carbamoyl)methyl ester (Compound No. 1)

The compound, 3-benzyl-3-azabicylo[3.1.0]hex-6-yl-2-chloroacetamide, 150 mg, 0.65 mmole, 1 eq (prepared by reacting 3-benzyl-3-azabicylo[3.1.0]hex-6-yl amine with 2-chloroacetyl chloride. The compound 3-benzyl-3-azabicyclo[3.1.0]hex-6-ylamine, in turn, can be prepared following the procedure of T. F. Braish et al., Synlett 1996, 1100) was dissolved in xylene. To the reaction mixture, potassium iodide was added with subsequent addition of (2-methoxy-5-methylphenyl)-3-phenyl propanoic acid (230 mg, 0.85 mmole, 1.5 eq) and 1,8-diazabicyclo[5.4.0]undec-7-ene. The reaction mixture was refluxed for 2 hours. Xylene was removed under pressure and the residue was dissolved in dichloromethane. The organic compound was then purified through column chromatography using 60% ethyl acetate in hexane.

Yield=70% (300 mg)

$^1$HNMR (CDCl$_3$, δ): 6.73-7.23 (m, 13 Ar—H), 4.8 (t, 1 H), 4.41 (s, 1 H), 3.75 (s, 3 H), 3.56 (s, 2 H), 1.25-3.13 (m, 13 H)

M/Z=499 (M$^+$+1)

EXAMPLE 2

Preparation of 3-(2-benzyloxy-5-methylphenyl)-3-phenyl propanoic acid-(3-benzyl-3-azabicyclo[3.1.0]-hex-6-yl carbamoyl)-methyl ester. (Compound No. 2)

The compound, 3-benzyl-3-azabicyclo[3.1.0]hexa-6-yl-2-chloroacetamide, 150 mg, 0.565 mmole (prepared by reacting 3-benzyl-3-azabicylo[3.1.0]hex-6-yl amine with 2-chloroacetyl chloride. The compound 3-benzyl-3-azabicyclo [3.1.0]hex-6-yl amine, in turn, can be prepared by following the procedure of T. F. Braish et al., Synlett 1996, 1100) was dissolved in xylene. To the reaction mixture, potassium iodide was added with subsequent addition of (2-benzyloxy-5-methylphenyl)-3-phenyl propanoic acid (294 mg, 0.85 mmole, 1.5 eq.) and 1,8-diazabicyclo[5.4.0]undec-7-ene. The reaction mixture was refluxed for 2 hrs. Xylene was removed under pressure and the residue was dissolved in dichloromethane. The organic compound was purified through column chromatography using ethyl acetate in hexane solvent system.

Yield=71.6% (300 mg)
IR (DCM, cm$^{-1}$): 1685; 1744
$^1$H NMR (CDCl$_3$, δ): 6.73-7.38 (m, 18 Ar—H), 4.95 (t, 1 H), 4.47 (s, 2 H), 3.53 (s, 2 H), 1.26-3.13 (m, 14 H)
M/Z: 575.1 (M$^+$+1)

EXAMPLE 3

Preparation of N-(3-azabicyclo[3.1.0]hex-6-yl)-3-(2-hydroxy-5-methylphenyl)-3-phenyl-1-propanoic acid. (Compound No.3)

Step a: The compound, 2-hydroxy-5-methylphenyl-3-phenyl-propanoic acid (520 mg, 2 mmole) was dissolved in dimethylformamide (9 ml). To the reaction mixture, 3-benzyl-3-azabicyclo[3.1.0]hex-6-yl amine (prepared following the procedure of T. F. Braish et. al., Synlett 1996, 1100) (376 mg, 2 mmole) was added and the resulting reaction mixture was cooled to 0° C. To this, N-methyl morpholine (0.265 ml) and 1-hydroxy benzotriazole, HOBT (337 mg) were added and stirred for 10 minutes at 0° C. Finally, 1-(3-dimethylamino propyl)-3-ethyl-carbodiimide hydrochloride was added and the reaction mixture was stirred for 30 minutes at 0° C. and brought to room temperature. The reaction mixture was diluted with water and the compound, N-(3-benzyl-3-azabicyclo[3.1.0]hex-6-yl)-3-(2-hydroxy-5-methylphenyl)-3-phenyl-propionamide was extracted with ethyl acetate, dried over sodium sulphate and concentrated under reduced pressure. The organic compound was purified through column chromatography using 70% ethylacetate in hexane as eluent.

Yield=62% (531 mg)
IR (KBr, cm$^{-1}$)=1631
M/Z=427 (M$^+$+1)

Step b: The compound, N-(3-benzyl-3-azabicyclo[3.1.0] hex-6-yl)-3-(2-hydroxy-5-methylphenyl)-3-phenyl-propionamide (200 mg, 0.47 mmole, 1 eq) was dissolved in methanol (25 ml) and 10% palladium on carbon (50 mg) was added. The reaction mixture was hydrogenated for 2 hrs at 50 Psi. The reaction mixture was filtered over celite pad, the filtrate was concentrated and dissolved in dichloromethane. It was washed with brine, dried over sodium sulphate and concentrated under reduced pressure to yield the title compound.

Yield=84.7% (133 mg)
IR(cm$^{-1}$)=1648
$^1$H NMR (CDCl$_3$, δ): 6.67-7.28 (m, 8 Ar—H), 6.67 (s, 1 H), 4.86 (t, 1 H), 1.25-3.14 (m, 12 H)
M/Z=336 (M$^+$+1)

EXAMPLE 4

Preparation of N-(3-azabicyclo[3.1.0]hex-6-yl)-3-(2-methoxy-5-methylphenyl)-3-phenyl-1-propionamide (Compound No. 4)

Step a: The compound, 2-methoxy-5-methylphenyl-3-phenyl propanoic acid (270 mg, 1 mmole, 1 eq) was dissolved in dimethylformamide. To the reaction mixture, 3-benzyl-3-azabicyclo[3.1.0]hex-6-yl-amine (prepared following the procedure of T. F. Braish et. al., Synlett 1996, 1100) (188 mg, 1 mmole) was added and the resulting reaction mixture was cooled to 0° C. To this, N-methyl morpholine (0.132 ml) and hydroxy benzotriazole (163 mg) were added and stirred for 10 minutes at 0° C. Finally, 1-(3-dimethylamino propyl)-3-ethyl-carbodiimide hydrochloride was added and the reaction mixture was stirred for 30 minutes at 0° C. and brought to room temperature. The reaction mixture was diluted with water and the compound, N-(3-benzyl-3-azabicyclo[3.1.0] hex-6-yl)-3-(2-methoxy-5-methylphenyl)-3-phenyl-propionamide was extracted with ethyl acetate, dried over sodium sulphate and concentrated. The purification was carried out through column chromatography using 60% ethyl acetate in hexane as eluent.

Yield=39% (170 mg)
IR(cm$^{-1}$)=1636
$^1$HNMR (CDCl$_3$, δ): 1.18 (s, 2 H), 3.75 (s, 3 H, —OCH$_3$), 6.73-7.3 (m, 13 ArH)
M/Z=441 (M$^+$+1)

Step b: The compound, N-(3-benzyl-3-azabicyclo[3.1.0] hex-6-yl)-3-(2-methoxy-5-methylphenyl)-3-phenyl propionamide was dissolved in methanol (15 ml), 200 mg of 10% palladium on carbon was added. The hydrogenation was continued for 4 hrs at 60 psi. The filtrate was concentrated and dissolved in dichloromethane, washed with brine and dried over sodium sulphate and concentrated under reduced pressure to yield the title compound.

Yield=75% (78 mg)
$^1$HNMR (CDCl$_3$, δ): 6.74-7.26 (m, 8 Ar—H), 6.71 (s, 1 H), 4.74-4.79 (t, 1H), 3.76 (s, 3 H), 1.11-3.05 (m, 12 H).

EXAMPLE 5

Preparation of 3-(2-methoxy-5-methylphenyl)-3-phenylpropanoic acid-4-[(3-azabicyclo[3.1.0]hex-6-yl]-ethoxy carbonylamino]butyl ester. (Compound No. 5)

Step a: The compound, 3-benzyl-3-azabicyclo[3.1.0]hex-6-yl-(4-bromobutyl)-carbamic acid t-butyl ester, 211.5 mg, 0.5 mmole, 1 eq (prepared by reacting boc-protected 3-benzyl-3-azabicylo[3.1.0]hex-6-yl amine, which in turn, was prepared following the procedure of T. F. Braish et al., Synlett, 1996, 1100, with 1-bromo-3-chloropropane) was dissolved in xylene (15 ml). To the reaction mixture, 3-(2-methoxy-5-methylphenyl)-3-phenyl propionic acid (203 mg, 0.75 mmole, 1.5 eq) and 1,8-diazabicyclo[5.4.0]undec-7-ene (0.75 mmole, 1.5 eq) were added. The resulting reaction mixture was refluxed for 2 hrs. Xylene was removed under reduced pressure and the residue was purified by column chromatography by using ethyl acetate in hexane solvent system to yield the compound, 3-(2-methoxy-5-methylphenyl)-3-phenyl propionic acid 4-[(3-benzyl-3-azabicyclo [3.1.0]hex-6-yl)-ethoxy carbonylamino]butyl ester.

Step b: The compound obtained above was dissolved in methanol (30 ml). To this, palladium on carbon (10%) was added. The resulting reaction mixture was hydrogenated at 60 psi for 4 hrs. The reaction mixture was filtered over celite pad. The filtrate was dried, concentrated to yield the title compound.

Yield=78.7% (141 mg)
IR (DCM, cm$^{-1}$)=1694, 1734
$^1$HNMR (CDCl$_3$, δ): 6.71-7.26 (m, 8 Ar—H), 4.86-4.92 (t, 1 H), 3.97-3.98 (t, 2 H), 3.74 (s, 3 H), 1.11-3.49 (m, 27 H)

EXAMPLE 6

Preparation of 3-(2-hydroxy-5-methylphenyl)-3-phenylpropionic acid 4-[(3-azabicyclo[3.1.0]hex-6-yl)ethoxyamino]butyl ester (Compound No. 6)

Step a: The compound, 3-benzyl-3-azabicyclo[3.1.0]hex-6-yl-(4-bromobutyl)-carbamic acid t-butyl ester, 211.5 mg, 0.5 mmole, 1 eq (prepared by reacting boc-protected 3-benzyl-3-azabicyclo[3.1.0]hex-6-yl amine, which in turn, was prepared following the procedure of T. F. Braish et al., Synlett, 1996, 1100, with 1-bromo-3-chloropropane) was dissolved in xylene (15 ml). To this reaction mixture, 3-(2- benzyloxy-5-methylphenyl) 3-phenyl propionic acid (260 mg, 0.75 mmole, 1.5 eq) and 1,8-diazabicyclo[5.4.0]undec-7-ene (0.75 mmole, 1.5 eq) were added. The resulting reaction mixture was refluxed for 2 hrs. Xylene was removed under reduced pressure and the residue was purified by column chromatography by using ethyl acetate in hexane solvent system to yield the organic compound, 3-(2-benzyloxy-5-methylphenyl)-3-phenyl propionic acid 4-[(3-benzyl-3-azabicylo[3.1.0]hex-6-yl)-ethoxy carbonylamino]butyl ester.

Step b: The compound obtained above (323 mg, 0.47 mmole, 1 eq) was dissolved in methanol (20 ml) with the subsequent addition of palladium on carbon (10%). The reaction mixture was hydrogenated at 60 psi for 3 hrs. The reaction mixture was filtered over celite pad and the filtrate was concentrated and dried to yield the desired product.

Yield=84% (200 mg)
IR (DCM, cm$^{-1}$)=1665, 1734
$^1$HNMR(CDCl$_3$, δ): 6.74-7.34 (m, 8 Ar—H), 4.86-4.92 (t, 1 H), 3.99-4.08 (t, 4 H), 1.10-3.85 (m, 27 H)

EXAMPLE 7

Preparation of 3-(2-methoxy-5-methylphenyl)-3-phenylpropionic acid-(3-azabicyclo[3.1.0]hex-6-yl carbamoyl)methyl ester (Compound No. 7)

The compound, 3-(2-methoxy-5-methylphenyl)-3-phenylpropionic acid-(3-benzyl-3-azabicyclo[3.1.0]hexan-6-yl-carbamoyl)methyl ester (193 mg, 0.39 mmole, 1 eq) as prepared in Example 1 was dissolved in methanol (20 ml) with subsequent addition of palladium on carbon (150 mg of 10%). The reaction mixture was hydrogenated at 60 psi for 3.5 hours at room temperature. Then, the reaction mixture was filtered over a celite pad and the clear filtrate was concentrated and dried to yield the product. Yield=70% (110 mg)

IR (KBr, cm$^{-1}$)=1675, 1746
$^1$HNMR (CDCl$_3$, δ): 6.74-7.31 (m, 8 Ar—H), 4.90-4.93 (t, 1 H), 4.44-4.52 (s, 1 H), 3.78 (s, 3 H), 1.26-3.50 (m, 14 H).

EXAMPLE 8

Preparation of 3-(2-hydroxy-5-methylphenyl)-3-phenylpropionic acid-(3-azabicyclo[3.1.0]hex-6-yl carbamoyl)methyl ester (Compound No. 8)

The compound, 3-(2-benzyloxy-5-methylphenyl)-3-phenyl propionic acid-(3-benzyl-3-azabicyclo[3.1.0]hex-6-yl carbamoyl)methyl ester (269 mg, 0.47 mmole, 1 eq) as prepared in Example 2 was hydrogenated with the same procedure as in Example 7 to yield the title compound.

IR (DCM, cm$^{-1}$): 1658, 1733
$^1$HNMR (CDCl$_3$, δ): 6.64-7.25 (m, 8 Ar—H), 4.75-4.78 (t, 1 H), 1.18-4.20 (m, Ar—H)

EXAMPLE 9

Preparation of N-[(3-benzyl-3-azabicyclo[3.1.0]hex-6-yl carbamoyl)-methyl]-3-(2-hydroxy-5-methylphenyl)-3-phenyl-propionamide (Compound No. 9)

The compound, 3-(2-hydroxy-5-methylphenyl)-3-phenyl propionic acid (198 mg, 0.77 mmole, 1 eq) and 2-amino-N-(3-benzyl-3-azabicyclo[3.1.0]hex-6-yl)-acetamide, 200 mg, 0.179 mmole, 1 eq prepared by reacting t-butoxy carbonylamino-acetic acid with 3-benzyl-3-azabicylo[3.1.0]hex-6-yl amine, which in turn, was prepared following the procedure of T. F. Braish et al., Synlett, 1996, 1100) were dissolved in dimethylformamide (3 ml). The reaction mixture was cooled to 0° C. with subsequent addition of N-methyl morpholine (2.31 mmole, 3 eq) and HOBT (0.77 mmole, 1 eq). The resulting reaction mixture was stirred for 1 hour at the same temperature and then at room temperature. The reaction mixture was diluted with water and extracted the organic compound with ethyl acetate. The solvent was removed under reduced pressure and dried. The crude compound was purified by column chromatography using ethyl acetate, methanol and dichloromethane solvent system.

Yield=12% (45 mg)
$^1$H NMR (CDCl$_3$, δ): 1.33 (s, 2 H), 2.14 (s, 3 H, —CH$_3$), 2.4 (d, 2 H, —NCH$_2$), 3.12 (d, 5 H), 3.55 (s, 2 H, NCH$_2$), 3.72 (s, 2 H, —NCH$_2$), 4.83 (t, 1 H), 6.6-7.26 (m, 13 ArH).

EXAMPLE 10

Preparation of N-[(3-benzyl-3-azabicyclo[3.1.0]hex-6-yl carbamoyl]-methyl]-3(-2-methoxy-5-methylphenyl)-3-phenyl propionamide (Compound No. 10)

The compound, 3-(2-methoxy-5-methylphenyl)-3-phenyl propionic acid (209 mg, 0.77 mmole, 1 eq) and 2-amino-N-(3-benzyl-3-azabicyclo[3.1.0]hex-6-yl)-acetamide, 0.77 mmole, 1 eq (prepared by reacting t-butoxy carbonyl aminoacetic acid with 3-benzyl-3-azabicylo[3.1.0]hex-6-yl amine, which in turn, was prepared following the procedure of T. F. Braish et al., Synlett 1996, 1100) were dissolved in dimethylformamide (5 ml). The reaction mixture was cooled to 0° C. with subsequent addition of N-methyl morpholine (0.13 ml) and 1-hydroxy benzotriazole, HOBT (105 mg). The resulting mixture was diluted with water and extracted the organic compound with ethyl acetate. The solvent was removed under reduced pressure. The crude organic compound thus obtained was purified by column chromatography using 80% ethyl acetate in hexane. Yield=367 mg.

$^1$H NMR (CDCl$_3$ δ): 6.72-7.29 (m, 13 ArH), 4.41(t, 1 H), 3.73(s, 3 H, OCH$_3$), 3.52 (s, 2 H).

EXAMPLE 11

Preparation of N-(3-benzyl-3-azabicyclo[3.1.0]hex-6-yl)-3-(2-hydroxy-5-methylphenyl)-3-phenyl propionamide. (Compound No. 11)

The compound, 3-(2-hydroxy-5-methylphenyl)-3-phenyl propionic acid (512 mg, 2 mmole, 1 eq) and 3-benzyl-3-azabicyclo[3.1.0]hex-6-yl amine, 376 mg, 2 mmole, 1 eq (prepared following the procedure of T. F. Braish et al., Synlett 1996, 1100) were dissolved in dimethylformamide and cooled to 0° C. To the reaction mixture, N-methyl morpholine (2.4 mmole, 1.2 eq) and 1-hydroxy benzotriazole, HOBT (2.2 mmole, 1.1 eq) were added. Finally, to the reaction mixture EDC. HCl (460 mg, 2.4 mmole, 1 eq) was added. The reaction mixture was stirred for 1 hour at 0° C. and then at room temperature. The reaction mixture was diluted with water, and the organic compound was extracted with ethyl acetate, dried over sodium sulphate and concentrated under high vacuum. The crude compound was purified by column chromatography using 40% ethyl acetate in hexane.

Yield=42.25% (360 mg)
IR (DCM, cm$^{-1}$)=1631
$^1$H NMR (CDCl$_3$, δ): 1.25 (s, 2 H), 2.1 (s, 3 H), 2.37 (d, 2 H), 3.00 (m, 5 H), 3.59 (5, 2 H), 4.87 (m, 1 H), 6.63-8.00 (m, 13Ar—H)

EXAMPLE 12

Preparation of 3-(2-methoxy-5-methylphenyl)-3-phenylpropionic acid-4-[(3-benzyl-3-azabicyclo[3.1.0]hex-6-yl)-ethoxy carbonylamino]butyl ester (Compound No. 12)

This compound was prepared as described in step (a) of Example 5.
Yield=98% (300 mg)
IR (DCM, $cm^{-1}$)=1688, 1730
$^1$HNMR (CDCl$_3$, δ): 6.70-7.27 (m, 13 Ar—H), 4.88 (t, 1 H), 3.94-3.96 (t, 2 H), 3.73 (s, 3 H), 3.56 (s, 2 H), 1.43-3.10 (m, 25 H)

EXAMPLE 13

Preparation of 3-(2-benzyloxy-5-methylphenyl)-3-phenyl propionic acid-4-[(3-benzyl-3-azabicyclo[3.1.0]hex-6-yl)-ethoxy carbonyl amino]butyl ester (Compound No. 13)

This compound was prepared in the same way as step (a) of Example 5 by using 3-(2-benzyloxy-5-methylphenyl)-3-phenyl propionic acid (260 mg, 0.75 mmole, 1.5 eq) instead of 3-(2-methoxy-5-methylphenyl)-3-phenyl propionic acid.
Yield=100% (445 mg)
IR (DCM, $cm^{-1}$)=1686, 1729
$^1$HNMR(CDCl$_3$, δ): 6.78-7.31 (m, 18 Ar—H), 5.00 (s, 2 H), 4.99 (t, 1 H), 3.90 (s, 3.57 (s, 2 H), 1.27-3.11 (m, 27 H).

EXAMPLE 14

Prepration of N-(3-benzyl-3-azabicyclo[3.1.0]hex-6-yl)-3-(2-methoxy-5-methylphenyl)-3-phenylpropionamide (Compound No. 14)

The compound, N-(3-benzyl-3-azabicyclo[3.1.0]hex-6-yl)-3-(2-methoxy-5-methylphenyl)-3 phenyl-propionamide was prepared in a same way as in Example 11 by using 3-(2-methoxy-5-methylphenyl)-3-phenyl-propionic acid (270 mg, 1 mmole, 1 eq) instead of 3-(2-hydroxy-5-methylphenyl)-3-phenyl propionic acid.
Yield=39% (170 mg)
(M/Z)=441(M$^+$)
$^1$H NMR (CDCl$_3$, δ): 1.18 (s, 2 H), 3.75 (t, 3 H, OCH$_3$), 6.73-7.3 (m, 13 ArH).

EXAMPLE 15

Preparation of (R or S)—N-(3-benzyl-3-azabicyclo[3.1.0]hex-6-yl]-[3-(2-methoxy-5-methylphenyl)-3-phenyl propyl]amine (Compound No. 15)

The compound, toluene-4-sulphonic acid-3-(2-methoxy-5-methylphenyl)-3-phenylpropyl ester (prepared as described in EP 0325571, 1.5 gm, 3.66 mmole, 1 eq) was dissolved in dry acetonitrile (4 ml). To the reaction mixture, 3-benzyl-3,6-diazabicyclo[3.1.0]hex-6-yl amine, 1.38 gm, 7.32 mmole, 2 eq, (prepared according to T. F. Braish et al. Synlett 1996, 1100) and triethylamine (5.1 ml) were added. The resulting reaction mixture was heated at 80° C. for 4 days. The solvents were evaporated off, from the reaction mixture under reduced pressure. The residue was dissolved in ethyl acetate, and washed with saturated sodium bicarbonate solution. The organic layer was separated, dried over sodium sulphate and concentrated under high vaccum. The crude compound was purified through column chromatography using ethyl acetate in hexane solvent system.
Yield=367 mg.
$^1$H NMR (CDCl$_3$, δ): 6.72-7.29 (m, 13 Ar—H), 4.41 (t, 1 H), 3.73 (s, 3 H) 3.52 (s, 2 H)

EXAMPLE 16

Preparation of (R or S)—N-(3-benzy-1-3-azabicyclo[3.1.0]hex-6-yl]-[3-(2-hydroxy-5-methylphenyl)-3-phenyl propyl]amine (Compound No.16)

This compound was prepared following the procedure as described in Example 15 by using toluene-4-sulphonic acid-3-(2-hydroxy-5-methylphenyl)-3-phenylpropyl ester instead of toluene-4-sulphonic acid-3-(2-methoxy-5-methylphenyl)-3-phenylpropyl ester.

Biological Activity

Radioligand Binding Assays:

The affinity of test compounds for $M_2$ and $M_3$ muscarinic receptor subtypes was determined by [$^3$H]—N-methyl scopolamine binding studies using rat heart and submandibular gland, respectively as described by Moriya et al., (Life Sci, 1999, 64(25): 2351-2358).

Membrane preparation: Submandibular glands and heart were isolated and placed in ice cold homogenizing buffer (HEPES 20 mM, 10 mM EDTA, and pH 7.4) immediately after sacrifice. The tissues were homogenized in 10 volumes of homogenizing buffer and the homogenate was filtered through two layers of wet gauze and filtrate was centrifuged at 500 g for 10 min. The supernatant was subsequently centrifuged at 40.000 g for 20 min. The pallet thus obtained was resuspended in same volume of assay buffer (HEPES 20 mM, EDTA 5 mM, pH 7.4) and were stored at –70° C. until the time of assay.

Ligand binding assay: The compounds were dissolved and diluted in dimethylsulfoxide. The membrane homogenates (150-250 µg protein) were incubated in 250 ul of assay buffer HEPES 20 mM, pH 7.4) at 24-25° C. for 3 hour. Non-specific binding was determined in the presence of 1 µM atropine. The incubation was terminated by vacuum filtration over GF/B fiber filters (Wallac). The filters were then washed with ice-cold 50 mM Tris HCl buffer (pH 7.4). The filter mats were dried and bound radioactivity retained on filters was counted. The IC$_{50}$ & Kd were estimated by using the non-linear curve-fitting program using G Pad Prism software. The value of inhibition constant Ki was calculated from competitive binding studies by using Cheng & Prusoff equation (Biochem Pharmacol, 1973.22: 3099-3108), Ki=IC$_{50}$/(1+L/Kd), where L is the concentration of [$^3$H]NMS used in the particular experiment.

$$pKi = -\log Ki$$

Functional Experiments using Isolated Rat Bladder:

Methodology:

Animals were euthanized by overdose of urethane and whole bladder was isolated and removed rapidly and placed in cold Tyrode buffer with the following composition (mMol/L) sodium chloride 137; KCl 2.7, CaCl$_2$ 1.8, MgCl$_2$ 0.1; NaHCO$_3$ 11.9, NaH$_2$PO$_4$ 0.4; Glucose 5.55 and continuously gassed with 95% O$_2$ and 5% CO$_2$ The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period, the stabilization of the tissue contractile response was assessed with 1 u mol/L of carbachol consecutively for 2-3 times. Subsequently, a cumulative concentration response curve to carbachol ($10^{-9}$ mol/L to $3\times10^{-5}$ mol/L) was obtained. After several washes, once the baseline was achieved, cumulative concentration response curve was obtained in the presence of NCE (NCE added 20 min. prior to the second CRC).

The contractile results were expressed as % of control E max ED50 values were calculated by fitting a non-linear regression curve (Graph Pad Prism). PKB values were calculated by the formula pKB=–log [(molar concentration of antagonist/(dose ratio-1))] where, dose ratio=ED50 in the presence of antagonist/ED50 in the absence of antagonist. The results of in-vitro test are listed in Table-II.

TABLE-II

| Compound No. | Receptor Binding Assay | | Functional Assay pKB |
|---|---|---|---|
| | $M_2$ pKi | $M_3$ pKi | |
| 1 | <6 | <6 | 5.01 |
| 2 | <6 | <6 | 5.17 |
| 3 | <6 | <6 | 5.95 |
| 4 | <6 | <6 | 5.64 |
| 5 | <6 | <6 | 5.15 |
| 6 | <6 | <6 | 5.84 |
| 7 | <6 | <6 | 5.6 |
| 8 | <6 | <6 | No blockade |
| 9 | <6 | <6 | 5.72 |
| 10 | <6 | <6 | 5.71 |
| 11 | <6 | <6 | 5.17 |
| 12 | <6 | <6 | 6.72 |
| 13 | — | — | — |
| 14 | — | — | — |
| 15 | — | — | — |
| 16 | — | — | 7.25 ± 0.15 |
| Tolterodine | 8.68 | 8.47 | 8.86 ± 0.12 |

While the present invention has been described in terms of its specific embodiments, certain modifications and equivalents will be apparent to those skilled in the art and are intended to be included within the scope of the present invention.

What is claimed is:

1. Compounds having the structure of Formula I

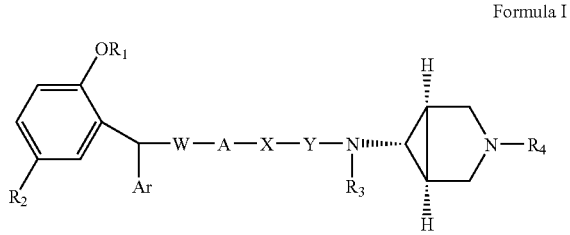

Formula I and their pharmaceutically acceptable salts, pharmaceutically acceptable enantiomers, diastereomers, or N-oxides, wherein Ar represents an aryl or a heteroaryl ring having 1-2 hetero atoms selected from the group consisting of oxygen, sulphur or nitrogen atoms, the aryl or heteroaryl rings may be unsubstituted or substituted by one to three substituents independently selected from lower alkyl ($C_1$-$C_4$), trifluoromethyl, methylenedioxy, cyano, hydroxy, halogen (e.g. F, Cl, Br, I), nitro, lower alkoxy ($C_1$-$C_4$), amino or lower alkylamino ($C_1$-$C_4$);

$R_1$ represents hydrogen, lower alkyl ($C_1$-$C_4$), lower alkenyl ($C_1$-$C_4$), lower alkynyl ($C_1$-$C_4$), aryl or aralkyl;

$R_2$ represents hydrogen or lower alkyl ($C_1$-$C_4$);

A represents $(CH_2)_n$ or CO, wherein n is an integer in the range of 0 to 4;

W represents $(CH_2)_p$, wherein p represents 1 to 4;

X represents O, S, NR or no atom, wherein R represents H or lower alkyl ($C_1$-$C_4$);

Y represents $CHR_5CO$, $(CH_2)_q$ or no atom, wherein $R_5$ represents hydrogen or methyl and q represents 1 to 4; and $R_3$ and $R_4$ are independently selected from hydrogen, straight chain or branched alkyl ($C_1$-$C_4$), cycloallyl, $CO_2C(CH_3)_3$, optionally substituted aryl or aralkyl.

2. A compound selected from the group consisting of:

3-(2-Methoxy-5-methylphenyl)-3-phenylpropionic acid-(3-benzyl-3-azabicyclo[3.1.0]hex-6-yl-carbamoyl)methyl ester (Compound No. 1)

3-(2-Benzyloxy-5-methylphenyl)-3-phenylpropionic acid-(3-benzyl-3-azabicyclo[3.1.0]hex-6-yl carbamoyl) methyl ester (Compound No. 2)

N-(3-Azabicyclo[3.1.0]hex-6-yl)-3-(2-hydroxy-5-methylphenyl)-3-phenyl-1-propionic acid (Compound No. 3)

N-(3-Azabicyclo[3.1.0]hex-6-yl)-3-(2-methoxy-5-methylphenyl)-3-phenyl-1-propionamide (Compound No.4)

3-(2-Methoxy-5-methylphenyl)-3-phenylpropionic acid-4-[(3-azabicyclo[3.1.0]hex-6-yl)-ethoxy carbonylamino]butyl ester (Compound No. 5)

3-(2-Hydroxy-5-methylphenyl)-3-phenylpropionic acid-4-[(3-azabicyclo[3.1.0]hex-6-yl)-ethoxy carbonylamino]butyl ester (Compound No. 6)

3-(2-Methoxy-5-methylphenyl)-3-phenylpropionic acid-(3-azabicyclo[3.1.0]hex-6-yl carbamoyl)methyl ester (Compound No. 7)

3-(2-Hydroxy-5-methylphenyl)-3-phenylpropionic acid-(3-azabicyclo[3.1.0]hex-6-yl carbamoyl)methyl ester (Compound No. 8)

N-[(3-Benzyl-3-azabicylo[3.1.0]hex-6-yl carbamoyl)-methyl]-3-(2-hydroxy-5-methylphenyl)-3-phenyl propionamide (Compound No. 9)

N-[(3-Benzyl-3-azabicyclo[3.1.0]hex-6-yl carbamoyl]-methyl]-3-(2-methoxy-5-methylphenyl)_3-phenyl propionamide (Compound No. 10)

N-(3-Benzyl-3-azabicyclo[3.1.0]hex-6-yl)-3-(2-hydroxy-5-methylphenyl)-3-phenyl propionamide (Compound No. 11)

3-(2-Methoxy-5-methylphenyl)-3-phenylpropionic acid-4-[(3-benzyl-3-azabicyclo[3.1.0]hex-6-yl)ethoxy carbonylamino]butyl ester (Compound No. 12)

3-(2-Benzyloxy-5-methylphenyl)-3-phenylpropionic acid-4-[(3-benzyl-3-azabicyclo[3.1.0]hex-6-yl)-ethoxy carbonylamino]butyl ester (Compound No. 13)

N-(3-Benzyl-3-azabicyclo[3.1.0]-hex-6-yl)-3-(2-methoxy-5-methylphenyl)-3-phenyl propionamide (Compound No. 14)

(R or S)—N-(3-Benzyl-3-azabicyclo[3.1.0]hex-6-yl)-3-[3-(2-methoxy-5-methylphenyl)-3-phenyl propyl] amine (Compound No. 15); and (R or S)—N-(3-Benzyl-3-azabicyclo[3.1.0]hex-6-yl)-3-[3-(2-hydroxy-5-methylphenyl]-3-phenyl propyl] amine (Compound No. 16).

3. A pharmaceutical composition comprising a pharmaceutically effective amount of a compound as defined in claim 1 or 2 optionally together with pharmaceutically acceptable carriers, excipients or diluents.

4. A method for treatment of an animal or a human suffering from a disease or disorder of the respiratory, urinary and gastrointestinal systems,
wherein the disease or disorder is urinary incontinence, lower urinary tract symptoms (LUTS), bronchial asthma, chronic obstructive pulmonary disorders (COPD), pulmonary fibrosis, irritable bowel-syndrome. Obesity, diabetes, and gastrointestinal hyperkinesis;
comprising administering to said animal or human, a therapeutically effective amount of a compound having the structure of Formula I,

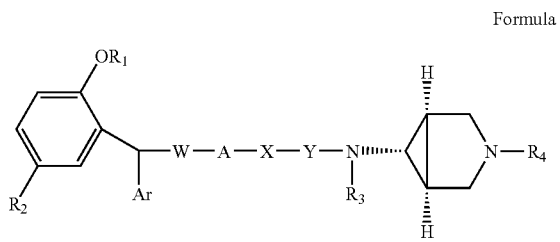

Formula I and its pharmaceutically acceptable salts, pharmaceutically acceptable enantiomers, diastereomers, or N-oxides, wherein
Ar represents an aryl or a heteroaryl ring having 1-2 hetero atoms selected from the group consisting of oxygen, sulphur or nitrogen atoms, the aryl or heteroaryl rings may be unsubstituted or substituted by one to three substituents independently selected from lower alkyl ($C_1$-$C_4$), trifluoromethyl, methylenedioxy, cyano, hydroxy, halogen (e.g. F, Cl, Br, I), nitro, lower alkoxy ($C_1$-$C_4$), amino or lower alkylamino ($C_1$-$C_4$);
$R_1$ represents hydrogen, lower alkyl ($C_1$-$C_4$), lower alkenyl ($C_1$-$C_4$), lower alkynyl ($C_1$-$C_4$), aryl or aralkyl;
$R_2$ represents hydrogen or lower alkyl ($C_1$-$C_4$);
A represents $(CH_2)_n$ or CO, wherein n is an integer in the range of 0 to 4;
W represents $(CH_2)_p$, wherein p represents 1 to 4;
X represents O, S, NR or no atom, wherein R represents H or lower alkyl ($C_1$-$C_4$);
Y represents $CHR_5CO$, $(CH_2)_q$ or no atom, wherein $R_5$ represents hydrogen or methyl and q represents 1 to 4; and
$R_3$ and $R_4$ are independently selected from hydrogen, straight chain or branched alkyl ($C_1$-$C_4$), cycloalkyl, $CO_2C(CH_3)_3$, optionally substituted aryl or aralkyl.

5. The method for treatment of an animal or a human suffering from a disease or disorder of the respiratory, urinary and gastrointestinal systems,
wherein the disease or disorder is urinary incontinence. lower urinary tract symptoms (LUTS), bronchial asthma. chronic obstructive pulmonary disorders (COPD), pulmonary fibrosis, irritable bowel syndrome, obesity, diabetes and gastrointestinal hyperkinesis;
comprising administering to said animal or human, a therapeutically effective amount of the pharmaceutical composition according to claim 3.

6. A process of preparing compounds having the structure of Formula 1,

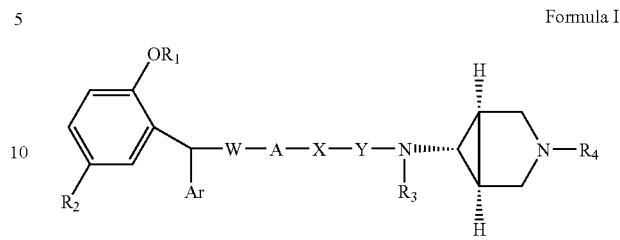

Formula I and their pharmaceutically acceptable salts, pharmaceutically acceptable enantiomers, diastereomers, or N-oxides, wherein
Ar represents an aryl or a heteroaryl ring having 1-2 hetero atoms selected from the group consisting of oxygen, sulphur or nitrogen atoms, the aryl or heteroaryl rings may be unsubstituted or substituted by one to three substituents independently selected from lower alkyl ($C_1$-$C_4$), trifluoromethyl, methylenedioxy, cyano, hydroxy, halogen (e.g. F, Cl, Br, I), nitro, lower alkoxy ($C_1$-$C_4$), amino or lower alkylamino ($C_1$-$C_4$);
$R_1$ represents hydrogen, lower alkyl ($C_1$-$C_4$), lower alkenyl ($C_1$-$C_4$), lower alkynyl ($C_1$-$C_4$), aryl or aralkyl;
$R_2$ represents hydrogen or lower alkyl ($C_1$-$C_4$);
A represents $(CH_2)_n$ or CO, wherein n is an integer in the range of 0 to 4;
W represents $(CH_2)_p$, wherein p represents 1 to 4;
X represents O, S, NR or no atom, wherein R represents H or lower alkyl ($C_1$-$C_4$);
Y represents $CHR_5CO$, $(CH_2)_q$ or no atom, wherein $R_5$ represents hydrogen or methyl and q represents 1 to 4; and
$R_3$ and $R_4$ are independently selected from hydrogen, straight chain or branched alkyl ($C_1$-$C_4$), cycloalkyl, $CO_2C(CH_3)_3$, optionally substituted aryl or aralkyl, comprising
a) condensing a compound of Formula II with a compound of Formula III,

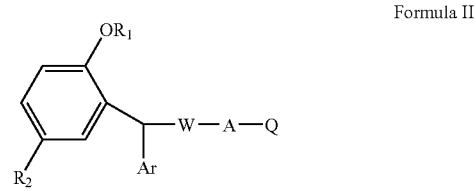

Formula II

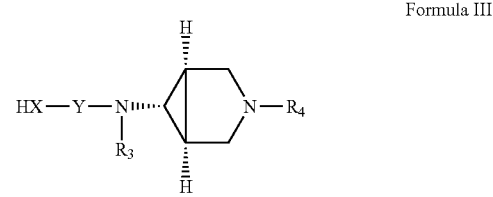

Formula III wherein Q is a leaving group and Ar, $R_1$, $R_2$, W, A, X, Y, $R_3$, $R_4$ are as defined earlier,
to give a compound of Formula IV wherein Ar, $R_1$, $R_2$, W, A, X, Y, $R_3$, $R_4$ are as Defined earlier, and

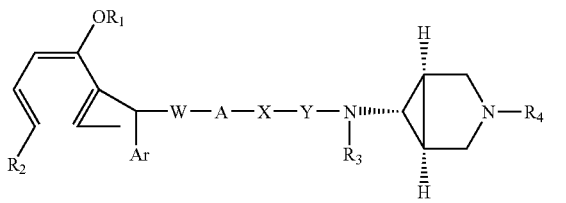

Formula IV b) deprotecting the compound of Formula IV in the presence of a deprotecting agent to give compounds of Formula I.

7. The process according to claim 6 wherein the leaving group Q is selected from the group consisting of hydroxy, amino, O-tosyl, O-mestyl and halogen.

8. The process according to claim 6 wherein the reaction of a compound of Formula II with a compound of Formula III to give compounds of Formula IV is carried out in the presence of a condensing agent selected from the group consisting of 1-(3-dimethylamino propyl)-3-ethyl-carbodiimide hydrochloride and 1,8-diazabicyclo[5.4.0]undec-7-ene.

9. The process according to claim 6 wherein the reaction of a compound of Formula II with a compound of Formula III to give compounds of Formula IV is carried out in a solvent selected from the group consisting of dimethylformamide, dimethylsulphoxide, toluene, xylene, methanol and dichloromethane.

10. The process according to claim 6 wherein the reaction of a compound of Formula II with a compound of Formula III to give compounds of Formula IV is carried out in the presence of a base selected from the group consisting of N-methyl morpholine, N-methyl-2-pyrrolidinone (NMP), sodium carbonate, potassium carbonate, triethylamine, Potassium iodide and diisopropylamine.

11. The process according to claim 6 wherein the reaction of a compound of Formula II with a compound of Formula III to give compounds of formula IV is carried out at a temperature ranging from about 0° C. to about 140° C.

12. The process according to claim 6 wherein the deprotection of a compound of Formula IV to give compounds of Formula I is carried out in the presence of a deprotecting agent selected from the group consisting of palladium on carbon, trifluoroacetic acid and hydrochloric acid.

* * * * *